United States Patent [19]
Lee et al.

[11] Patent Number: 6,147,266
[45] Date of Patent: Nov. 14, 2000

[54] METHOD FOR PRODUCING ACETYLENE ALCOHOL COMPOUNDS USING CONTINUOUS PROCESS

[75] Inventors: Si-Joon Lee; Chang-Kuk Kim; Young-Gyun Jung; Young-Sun Kang; Taik-Keun Kim, all of Taejon, Rep. of Korea

[73] Assignee: SK Corporation, Seoul, Rep. of Korea

[21] Appl. No.: 09/220,662

[22] Filed: Dec. 24, 1998

[30] Foreign Application Priority Data

Aug. 26, 1998 [KR] Rep. of Korea .................. 98-34685

[51] Int. Cl.⁷ .................................................. C07C 33/04
[52] U.S. Cl. ................................... 568/874; 568/855
[58] Field of Search ............................. 568/874, 855

[56] References Cited

U.S. PATENT DOCUMENTS

| | | | |
|---|---|---|---|
| 2,826,614 | 3/1958 | Whitefield | 568/874 |
| 3,105,098 | 9/1963 | Frantz | 568/885 |
| 3,801,653 | 4/1974 | Pasedach | 568/874 |

FOREIGN PATENT DOCUMENTS

| | | |
|---|---|---|
| 2131205 | 11/1972 | France . |
| 1223364 | 8/1966 | Germany . |
| 2126356 | 12/1972 | Germany . |

*Primary Examiner*—Michael L. Shippen
*Attorney, Agent, or Firm*—Seidel, Gonda, Lavorgna & Monaco, PC

[57] ABSTRACT

There is disclosed a method for producing acetylene alcohol compounds in a continuous process, which are produced via ethynylation in which ketones containing a group —$CH_2COCH_2$—, are condensed with acetylenes at a temperature of about 20 to 50° C. under a pressure of about 10 to 30 kg/cm² in the presence of a quaternary ammonium hydroxide anion exchange resin having strong basicity in an aprotic solvent by feeding a reactant mixture at an LHSV range of 0.1 to 5.0 and the reactant mixture comprises the acetylene, the ketone and the solvent at a molar ratio of 1.0:0.2–3.0:1.0–4.0.

11 Claims, 8 Drawing Sheets

METHOD FOR PRODUCING ACETYLENE ALCOHOL COMPOUNDS USING CONTINUOUS PROCESS

BACKGROUND OF THE INVENTION

1. Field of the Invention

The present invention relates to a method for producing acetylene alcohol compounds in a continuous type process using strong basic, heterogeneous anion exchange resins. More specially, the present invention relates to an ethynylation in which acetylene and ketone compounds are condensed in a continuous process in an aprotic solvent in the presence of quaternary ammonium hydroxide anion exchange resins, as represented by the following reaction formula I, thereby producing commercially useful acetylene alcohol compounds at high yields in an environmentally favorable fashion:

[Reaction Formula I]

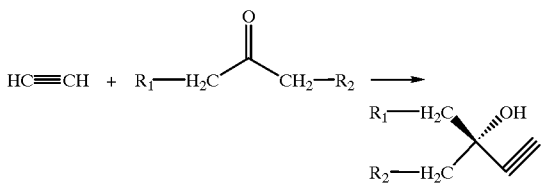

wherein $R_1$ and $R_2$, which may be the same or different, each is a hydrogen atom, a linear or branched, saturated or unsaturated alkyl containing 1 to 16 carbon atoms, or a linear or branched, saturated or unsaturated phenyl containing 1 to 16 carbon atoms.

2. Description of the Prior Art

Thus far, acetylene alcohol compounds have been prepared through the condensation of ketone and acetylene by the method which was developed by Favorskii. According to Favorskii's method, acetylene is converted into acetylide in the presence of a metal salt capable of deprotonation in liquid ammonia or another suitable solvent, followed by condensing the acetylide with appropriate ketones to provide desired acetylene alcohol compounds. Besides liquid ammonia, ethers are usually used as the solvents. As for the catalysts carrying out the condensation reaction, they comprise metal salts of strong base, e.g, alkaline metal hydroxides, and particularly, potassium hydroxide is usually used.

This method is, however, found to be disadvantageous in several points. First, excess amounts of alkaline metal hydroxide should be used. That is, stoichiometric to excess amounts of metal hydroxides compound to ketones must be used, and this results in a considerable inefficiency in economical and environmental aspects. One of the requirements which a good reaction must meet, is the minimization of undesirable by-products. However, the use of excess amounts of alkaline metal hydroxides induces production of by-products, resulting in a decrease in the production yield of the ultimate objects, acetylene alcohol compounds. Moreover, because the above acetylene alcohol production reaction is reversible, the conversion rate of ketones and the production yield of acetylene alcohols may be decreased during the separation and purification of the product at higher temperature in the presence of a catalyst.

On the basis of the experiment data established thus far, liquid ammonia is used as the most efficient solvent for the reaction in view of the production yield of the desired acetylene alcohol compounds and the conversion rate of ketones. To be used as a solvent, ammonia should be liquified, which requires a very low temperature and thus, a corresponding energy expenditure. In addition, the low temperature imposes a stiff burden on the recovery of the product. Moreover, liquid ammonia is unfavorable to the environment.

SUMMARY OF THE INVENTION

Thorough and intensive research repeated by the present inventors aiming to develop a method for producing acetylene alcohol compounds at high yields, has resulted in the finding that the ethynylation of ketones with acetylenes in an aprotic solvent in the presence of a quaternary ammonium hydroxide anion exchange resin having strong basicity under mild conditions can bring about a great improvement in the conversion rate of ketones and in the selectivity for acetylene alcohol compounds. The regeneration of the anion exchange resin allows the acetylene alcohol compounds to be produced continuously.

Therefore, it is an object of the present invention to provide a method for producing acetylene alcohol compounds under mild conditions in which no liquid ammonia and a minimal amount of alkali metal hydroxide are used, thereby greatly improving the production yield in an environmentally favorable fashion.

It is another object of the present invention to provide a method for producing acetylene alcohol compounds, which is applicable to commercial ends.

In accordance with the present invention, there is provided a method for producing an acetylene alcohol compound in a continuous process, wherein a ketone containing a group, $-CH_2COCH_2-$, is condensed to an acetylene at a temperature of about 20 to 50° C. under a pressure of about 10 to 30 kg/cm² in the presence of a quaternary ammonium hydroxide anion exchange resin having strong basicity in an aprotic solvent by feeding a reactant mixture at an LHSV range of 0.1 to 5.0, the reactant mixture comprising the acetylene, the ketone and the solvent at a molar ratio of 1.0:0.2–3.0:1.0–4.0.

BRIEF DESCRIPTION OF THE DRAWINGS

The above and other objects and aspects of the invention will become apparent from the following description of embodiments with reference to the accompanying drawings in which.

DETAILED DESCRIPTION OF THE INVENTION

Figure 1:
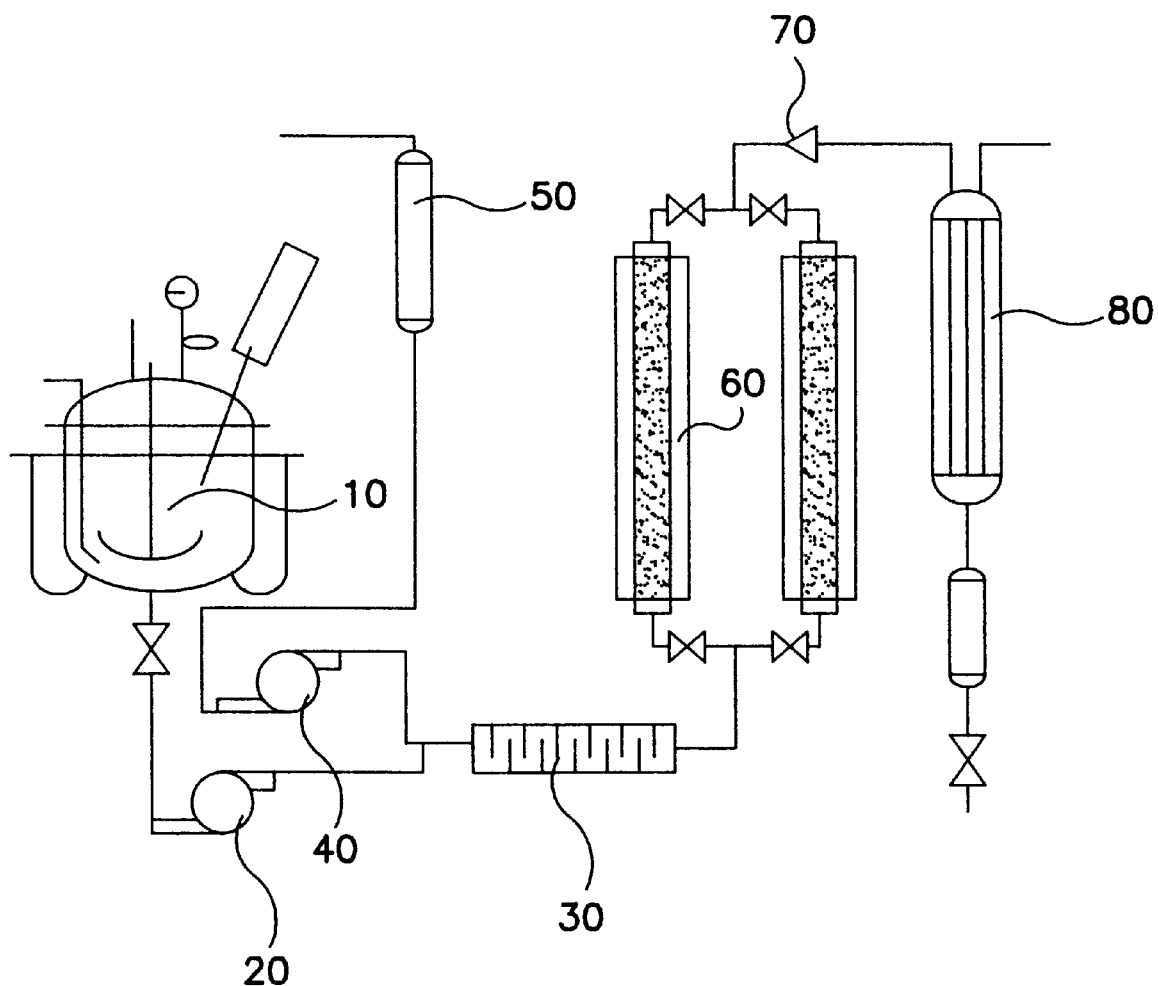
FIG. 1 is a schematic diagram showing an apparatus in which acetylene alcohol compounds can be produced in a continuous process, according to the present invention.

In the invention, an acetylene alcohol compound, represented by the following chemical formula I:

[Chemical Formula I]

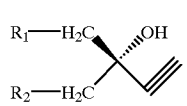

wherein R₁ and R₂, which may be the same or different, each is a hydrogen atom, a linear or branched, saturated or unsaturated alkyl containing 1 to 16 carbon atoms, or a linear or branched, saturated or unsaturated phenyl containing 1 to 16 carbon atoms, are prepared through the ethynylation in which an acetylene is condensed to a ketone containing the group —CH$_2$—CO—CH$_2$—, represented by the following chemical formula II:

[Chemical Formula I]

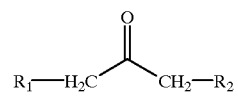

wherein R₁ and R₂ are as defined above.

Some examples of the acetylene alcohol compounds prepared according to the invention are listed according to their chemical structures, systematic names (IUPAC) and abbreviated names in Table 1. The corresponding ketones appear in Table 2, below.

TABLE 1

Acetylene Alcohol Compounds

| Nomenclature(IUPAC) | Chemical Structure | Abbr. |
|---|---|---|
| 2-Methyl-but-3-yn-2-ol | 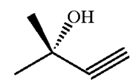 | DMEC |
| 3,7-Dimethyl-oct-6-en-1-yn-3-ol | 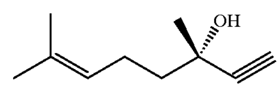 | DHL |
| 3,7,11-Trimethyl-dodeca-6,10-dien-1-yn-3-ol | 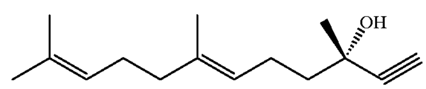 | DHN |
| 3,7,11,15-Tetramethyl-6,10,14-hexadecatrien-1-yn-3-ol | 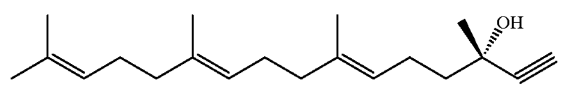 | GDHL |
| 3,7,11,15-Tetramethyl-hexadeca-1-yn-3-ol | 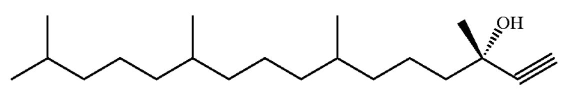 | DHiP |

TABLE 2

Ketones

| Nomenclature(IUPAC) | Chemical Structure | Abbr. |
|---|---|---|
| 2-Propanone | 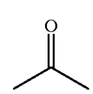 | Acetone |
| 6-Methyl-hept-5-en-2-one | 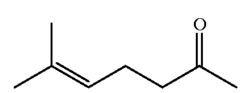 | MH |
| 6,10-Dimethyl-undeca-5,9-dien-2-one | 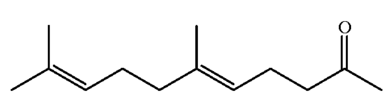 | GA |

TABLE 2-continued

Ketones

| Nomenclature(IUPAC) | Chemical Structure | Abbr. |
| --- | --- | --- |
| 6,10,14-Trimethyl-5,9,13-pentadecatrien-2-one | 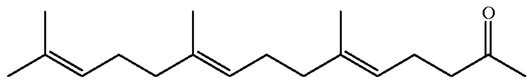 | FA |
| 6,10,14-Trimethyl-pentadecan-2-one | 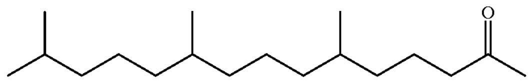 | PT |

Useful solvents for the ethynylation in the present invention are aprotic solvents which give a relatively high solubility for acetylene gas and somewhat of a degree of solubility for ketone. Preferred solvents are dimethylformamide (hereinafter referred to as "DMF"), dimethyl sulfoxide (hereinafter referred to as "DMSO") and N-methylpyrrolidone (hereinafter referred to as "NMP").

The condensation is carried out in the presence of a base. For this, a strong basic, quaternary ammonium hydroxide anion exchange resin, is employed in the invention. Commercially available examples include the products sold under the tradenames Amberlite IRA-402 (OH), 410 (OH) and 900 (OH) of Rohm & Hass and the products sold under the tradename AB-17-8 (OH) made in Russia. IRA-402 (OH), IRA-900 (OH) and AB-17-8 (OH) are preferred.

In order not to give a physically negative effect on the activity of the anion exchange resin, a milder temperature condition than those of conventional ethynylation processes is needed. In accordance with the present invention, the ethynylation is carried out at a temperature of 20 to 50° C. and preferably 30 to 40° C. For example, if the reaction temperature is below 20° C., the ethynylation proceeds little. On the other hand, if the reaction temperature is over 50° C., the anion exchange resin is likely to degrade.

The pressure ranges from 10 to 30 kg/cm$^2$ and preferably from 15 to 25 kg/cm$^2$. For example, if the ethynylation is carried out at below 10 kg/cm$^2$, the reaction proceeds too slowly. On the other hand, if the pressure is over 30 kg/cm$^2$, a physical deformation occurs on the anion exchange resin.

Referring to FIG. 1, there is shown the structure of an apparatus in which acetylene alcohol compounds can be produced in a continuous process, according to the present invention. Acetylene gas is saturated in a reaction solvent to give an acetylene solution to be used later, in a first reactor 10. This acetylene saturation is very important in carrying out the ethynylation of the invention. Dissolution of acetylene in the solvent may be accomplished by saturating acetylene gas in a cooled solvent under low pressure or by applying the gas under pressure into the reactor containing the solvent at an ordinary temperature or a saturation-desired temperature. Simultaneous operation of a stirrer is helpful in increasing the solubility of the acetylene to some extent.

Preferred conditions for the preparation of saturated acetylene solutions are given in Table 3, below.

TABLE 3

| Saturation Temp. (° C.) | Solvents | Saturation Press. (Kg/cm$^2$) |
| --- | --- | --- |
| −10~−20 | NMP, DMF | 0.5~2.0 |
| −5~0 | NMP, DMF | 4.0~9.0 |
| 23~25 | NMP, DMF, DMSO | 6.0~10.0 |

DMSO is excluded when the saturation is performed at low temperatures because it has a high melting point.

Turning now to FIG. 1, the acetylene saturated solution thus prepared is provided to a mixer 30 with the aid of a first metering pump 20. Simultaneously, a second metering pump 40 is operated to provide a ketone reactant to the mixer 30 in which the reactants are, then, mixed to a desired concentration. The resulting mixture is transferred to a second reactor 60 filled with anion exchange resins, in which condensation occurs under conditions set to a temperature of 20 to 50° C. and a pressure of 10 to 30 kg/cm$^2$. The pressure can be controlled with a valve 70. Unreacted acetylene, is removed from the reaction mixture for later reuse by a thin film evaporator 80.

Following neutralization by treatment with KHSO$_4$, the reactant mixture which remains unreacted is used to analyze the conversion rates of the ketones used in the reaction, and the corresponding selectivities for alcohols by, gas-liquid chromatography.

In an embodiment of the present invention, two reactors 60 which are filled with the anion exchange resin are arranged in parallel so that they are alternatively used for continuous processing. That is, when, during working, one of the reactors begin to show reduced anion exchange resin activity as measured by the conversion rate of ketone, the flow of the reactant mixture is directed to the other reactor 60, so that the condensation reaction continues to proceed. While one of the two reactors 60 is working, the other is regenerated, thereby efficiently producing the desired compounds.

Useful anion exchange resins in the present invention are those which have OH active groups. Commercially available resins having Cl active groups should first be converted to the hydroxide (OH) type before use. The procedure for this conversion is as follows: Cl type ion exchange resins are placed in the second reactor and treated with a 5 wt % solution of NaOH or KOH in methanol for a period of time, followed by flowing a reaction solvent for a period of time to replace the methanol solution.

After the anion exchange resins are introduced into the second reactor, the resins themselves volumetrically swell to an extent as the reaction proceeds. Thus, only up to 80 vol % of the reactor should be filled with the ion exchange resins in order to prevent a the pressure increase resulting from the volume expansion of the resins deleteriously affecting the reaction.

The ketones are used at an amount of 0.2 to 3.0 moles per mole of the acetylene, while the solvent ranges, in molar ratio, from 1.0 to 4.0.

To measure the effect of reaction time, the condensation was carried out in the wide LHSV (liquid hourly space velocity) range of 0.1 to 5.0. Herein, LHSV is the ratio of the volume of the reactant fed per hour to the volume of the catalyst filled in the reactor, as defined by the following mathematical equation I:

$$LHSV = \frac{\text{Vol. of Reactant Solution fed per hour}}{\text{Vol. of Catalyst}} \quad \text{[Mathematical equation I]}$$

After completion of the reaction, the desired products are isolated and purified through a series of processes, including removal of unreacted acetylene from the reactant mixture, extraction of the solvent, and distillation, fractional distillation or extraction according to the boiling points of the products.

A better understanding of the present invention may be obtained in light of following examples which are set forth to illustrate, but are not to be construed to limit, the present invention.

ION EXCHANGE RESIN TREATMENT EXAMPLE I

Ion Exchange Resin IRA-402 (OH)

40 ml of the anion exchange resin was filled in a tubular reactor 60 cm long with an inner diameter of 19 mm (see FIG. 1), followed by continuously flowing methanol for 20 to 25 hours into the reactor to remove the moisture present in the resin. Under the control of a metering pump, the methanol was introduced at an amount of 0.2 to 0.25 ml per hour per ml of ion exchange resin. The methanol which came out of the reactor was periodically analyzed for its moisture content. When the moisture content in the methanol was maintained at 0.3 wt % or less, the feed of the methanol was stopped. The methanol fractions passed out of the reactor were pooled and stored for reuse. Thereafter, a solvent to be used for acetylene saturation and condensation reaction was provided at a flow rate of 50 ml/hour for 10 hours with the aid of a metering pump, so as to wash the ion exchange resin.

ION EXCHANGE RESIN TREATMENT EXAMPLE II

Ion Exchange Resin IRA-900 (OH)

The resin was treated in the same manner as that of Treatment Example I.

ION EXCHANGE RESIN TREATMENT EXAMPLE III

Ion Exchange Resin IRA-410 (OH)

The resin was treated in the same manner as that of Treatment Example I.

ION EXCHANGE RESIN TREATMENT EXAMPLE IV

Ion Exchange Resin AB-17-8 (OH)

The resin was treated in the same manner as that of Treatment Example I.

ION EXCHANGE RESIN TREATMENT EXAMPLE V

Ion Exchange Resin IRA-402 (Cl)

40 ml of the anion exchange resin was filled in the same tubular reactor as that of Treatment Example I, followed by continuously flowing a 5 wt % solution of KOH or NaOH in methanol for 20 to 25 hours into the reactor to replace the Cl ions of the ion resin with OH ions. The solution was flowed under the control of a metering pump. After being dried at 50° C. under vacuum, the resin was re-washed with a solvent to be used for acetylene saturation and condensation reaction for 10 hours with the aid of a metering pump. The solvent was preferably flowed at a rate of 50 ml/hour.

ION EXCHANGE RESIN TREATMENT EXAMPLE VI

Ion Exchange Resin IRA-900 (Cl)

The resin was treated in the same manner as that of Treatment Example V.

ION EXCHANGE RESIN TREATMENT EXAMPLE VII

Ion Exchange Resin IRA-410 (Cl)

The resin was treated in the same manner as that of Treatment Example V.

ION EXCHANGE RESIN TREATMENT EXAMPLE VIII

Ion Exchange Resin AB-17-8 (Cl)

The resin was treated in the same manner as that of Treatment Example V.

ION EXCHANGE RESIN REGENERATION EXAMPLE I

When the conversion rate of ketone, after the condensation reaction proceeded for a period of time, was reduced to a predetermined level in comparison with that of the initial reaction stage, the reactant mixture feed was suspended in order to regenerate the ion exchange resins.

The restoration of the activity of the resins was obtain by continuously feeding a 5 wt % solution of KOH or NaOH in methanol while preferably maintaining the volume ratio of the ion exchange resins to the 5 wt % solution at 1:4. By using a metering pump, the alkali methanol solution was continuously provided at a flow rate of 20 to 50 ml/hour for 8 to 9 hours.

After completion of the regeneration, methanol was continuously introduced to the ion exchange resins to remove the alkali methanol solution present therein. When the eluant passed from the resins became neutral (about pH 7.0), the methanol introduction was stopped.

Thereafter, an aprotic solvent to be used for acetylene gas saturation was fed preferably at a flow rate of 50 ml/hour for 10 hours with the aid of a metering pump, so as to wash the ion exchange resins.

ACETYLENE SATURATED SOLUTION PREPARATION EXAMPLE

A predetermined amount of a solvent to be used was poured into the first high pressure reactor equipped with a stirrer, a manometer and a thermometer. The solvent was maintained at a desired temperature with the aid of a heating medium while stirring. Acetylene gas from a cylinder was added in bubble form to saturate the solvent at a desired concentration which was then maintained by applying the appropriate pressures of acetylene gas according to reaction temperatures. The content of acetylene in the reactant mixture was quantitatively measured by use of an Illosvay solution.

Analysis Principle

The quantitation of the dissolved acetylene was based on the reaction between the copper acetylide ($Cu_2C_2$) formed from acetylene and an acidic solution of ferric (III) salt, as shown in the following reaction formula II:

[Reaction Formula II]

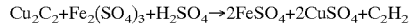

$$Cu_2C_2+Fe_2(SO_4)_3+H_2SO_4 \rightarrow 2FeSO_4+2CuSO_4+C_2H_2$$

The quantity of acetylene could be measured by titrating the formed ferrous (II) salt with a standard $KMnO_4$ solution. On the whole, one mole of $Cu_2C_2$ reacts correspondingly with two equivalents of $KMnO_4$. The free acetylene after the reaction has no affect on the titration.

Preparation of Analysis Reagents a) Standard acid solution of $Fe_2(SO_4)_3$ 100 g of $Fe_2(SO_4)_3$ was dissolved in 200 ml of conc. sulfuric acid, followed by adding distilled water to a final 1 liter volume.

b) Illosvay reagent

In a 50 ml flask was placed 0.75 g of $CuCl_2.3H_2O$ which was then well dissolved with a small amount of distilled water. 1.5 g of $NH_4Cl$ was added in the flask, followed by the slow addition of 3 ml of a 20 to 21 weight % aqueous solution of ammonia in water. The resulting mixture was well dissolved before the addition of distilled water to a final volume of 50 ml. At this time, the color of the solution disappeared.

Analysis Procedure i) 35 to 40 ml of a solvent (NMP, DMF or DMSO) in a flask was cooled down to 0 to 10° C. for NMP and DMF, or to 15 to 16° C. for DMSO, before 1 to 1.5 ml of a sample was dissolved. After dissolving each sample, the solution was weighed to an accuracy on the order of 0.01 g. Later, each was weighed again.

ii) While stirring the solution with care, 10 to 15 g of the solution was taken (with an accuracy on the order of 0.01 g) and then combined with about 20 to 25 ml of Illosvay reagent to give red colored $Cu_2C_2$ precipitates.

iii) After being collected with a glass filter in a nitrogen atmosphere to prevent acetylide contact with the air, the precipitates were thoroughly washed many times with distilled water (to completely remove hydroxyamine). The perfection of the washing could be recognized from the situation that, when a drop of the $KMnO_4$ solution was added, the solution remained red for 30 seconds or more.

iv) The precipitates were dissolved in 25 ml of the $Fe_2(SO_4)_3$ standard acidic solution to give a green solution which was then accurately titrated with 1N $KMnO_4$.

v) The acetylene content was calculated according to the following mathematical equation II:

$$\% \ C_2H_2 = \frac{260.4 \ VKP_o}{2000 \ P_s(P_1 - P_s)} \quad \text{[Mathematical equation II]}$$

wherein $P_o$ is the total weight of the solution (solvent+reaction mixture sample), $P_1$ is the weight of the net solvent (solution mixed upon extraction of sample), $P_s$ is the weight of the sample used for the Illosvay reaction, V is the volume of the $KMnO_4$ solution consumed for titration, K is a correction factor for the $KMnO_4$ solution.

EXAMPLE I

Effect Upon Reactant Mixture Composition

In the ethynylation of condensing acetylene to ketone according to the present invention, the relative concentrations of the reactants have a great influence on the conversion rate of ketone and the selectivity for the desired products, acetylene alcohol compounds. It is also well known that acetylene is limitatively saturated in a given volume of a solvent at a constant temperature under a constant pressure. Accordingly, the ethynylation results are greatly dependent on the molar ratio of acetylene to ketone.

In this example, the reaction results were monitored according to the change in the composition of the reactants, acetylene and ketone, and the solvents.

Into the reactor (60 cm long with an inner diameter of 19 mm) of the continuous process apparatus of FIG. 1 was filled 40 ml of anion exchange resin AB-17-8 (OH). This resin was treated in the same manner as that of Treatment Example IV, followed by slowly feeding the acetylene-saturated solution and ketone to the reactor. NMP was used as a reaction solvent. The saturation of acetylene was in the low temperature course (–10~–12° C.) shown in Table 3, above. The reaction was carried out at 40° C. under a pressure of 20 kg/cm² with acetone as the ketone reactant.

The reaction results are given in Table 4, below.

TABLE 4

| Test No. | Molar Ratio | | | LHSV | Conversion of Acetone (%) | Selectivity for DMEC (%) |
| --- | --- | --- | --- | --- | --- | --- |
| | Acetylene | Acetone | NMP | | | |
| 1 | 1.0 | 2.34 | 2.34 | 0.33 | 38.8 | >98 |
| 2 | 1.0 | 1.18 | 2.37 | 0.40 | 46.5 | >98 |
| 3 | 1.0 | 1.41 | 2.37 | 0.40 | 72.5 | >98 |
| 4 | 1.0 | 2.36 | 2.35 | 0.46 | 51.1 | >98 |
| 5 | 1.0 | 0.97 | 2.36 | 0.46 | 73.3 | >98 |
| 6 | 1.0 | 0.44 | 2.37 | 0.46 | 79.6 | >99 |
| 7 | 1.0 | 0.90 | 2.34 | 0.20 | 85.1 | >99 |
| 8 | 1.0 | 0.50 | 1.55 | 0.20 | 91.2 | >98 |

The selectivity for the product, 2-methyl-but-3-yn-2-ol (DMEC), was determined on the basis of the reacted amount of acetone by gas chromatography. In the reaction, LHSV and the molar ratio of acetylene to acetone to the solvent are used as variable parameters, whereas reaction temperature and pressure are constant parameters.

It is apparent from the data of Table 4 that the conversion rate of acetone increases as the stoichiometry of the acetone compared to the acetylene decreases if the other parameters, including LHSV, reaction temperature, pressure and moles of NMP, are held constant. This means that, because the amount of the acetylene saturated in a given volume of the solvent is constant under given conditions, the reaction proceeds better if the number of moles of acetone used is less than the number of moles of acetylene. Particularly, where the molar ratio of acetone to acetylene is below 1, the conversion rate of acetone is maintained at above 70%. The simple change of the solvent amount affects the saturation of the acetylene, but has no effect on the conversion rate of acetone, or the selectivity for DMEC. In contrast, when LHSV, which is connected with reaction time, was changed, different reaction results came about. The smaller the LHSV, that is, the smaller the amount of the treated reactants per volume of the ion exchange resin per hour, the greater the conversion rate of acetone. In other words, as the treatment time increases, the conversion rate of acetone increases.

Accordingly, it is thought that the ethynylation should be carried out at an LHSV of 0.5 or less and at a molar ratio of acetylene to acetone to solvent of 1.0:0.5–1.0:1.5–3.0 in order to maintain the conversion rate of acetone at 70% or more. Thus, unless particularly mentioned in subsequent relevant reactions, the molar ratio of acetylene to acetone to solvent is on the order of 1.0:0.5:1.5–2.5. Under this condition, the effects of the other parameters will be compared.

EXAMPLE II

Solvent Effect

The same procedure as in Example I was repeated, except that DMF, instead of NMP, was used as a solvent. Acetylene-saturated NMP solutions were prepared by following the instructions shown in Table 3, above. The data obtained through preparative experiments under the same reaction conditions, show that if acetylene is used at a constant amount, similar results attained for the conversion rate of ketone and for the selectivity for acetylene alcohol compound, each, irrespective of the kinds of solvent. The ethynylation was carried out in the same conditions, but with different solvents. The results were given in Table 5, below.

TABLE 5

| Solvent | Molar Ratio | | | LHSV | Conversion of Acetone (%) | Selectivity for DMEC (%) |
| --- | --- | --- | --- | --- | --- | --- |
| | Acetylene | Acetone | Sol. | | | |
| NMP | 1.0 | 0.5 | 1.55 | 0.2 | 91.2 | >98 |
| DMF | 1.0 | 0.5 | 1.55 | 0.2 | 90.0 | >98 |

As apparent from Table 5, merely varying the solvent within an aprotic solvent category has almost no effect on the conversion rate of acetone and the selectivity for DMEC. From this result, the solvents used in the invention are aprotic, with a preference for NMP, DMF and DMSO. In subsequent Examples, any solvent of NMP, DMF and DMSO may be employed.

EXAMPLE III
Effect Upon Change in LHSV

Generally, reaction time is an important parameter of a reaction. In this Example, the effect of changes in reaction time was obtained at various LHSV values. Information on the relation between the amounts of reactants and ion exchange resins is very important in performing the continuous process of the invention.

As mentioned above in equation I, LHSV is defined as the volume of reactant which is treated by a unit volume of catalyst for one hour. In order to consider the condensation of acetylene to ketone on reaction rate, the reaction results were monitored according to LHSV change. From the data of Test. Nos. 5 and 7 of Table 4 in Example I, it is known that an increase in LHSV causes a significant reduction in ketone conversion level if the composition comprising the reactants and the solvent is kept constant. Consequently, the larger the volume of reactants which is treated per hour by a unit volume of anion exchange resin, that is, the shorter the contact time between the anion exchange resin and the reactants, the lower the conversion level of ketone.

In order to confirm this result, the reactant mixture was flowed through anion exchange resin IRA-402 (OH) in an LHSV range of 0.1 to 0.5 while other parameters were kept constant. Some results are given in Table 6, below.

TABLE 6

| LHSV | Molar Ratio | | | Conversion of Acetone (%) | Selectivity for DMEC (%) |
| --- | --- | --- | --- | --- | --- |
| | Acetylene | Acetone | DMF | | |
| 4 | 1.0 | 0.5 | 1.92 | 56~74 | >98 |
| 1 | 1.0 | 0.5 | 1.92 | 69~78 | >98 |
| 0.5 | 1.0 | 0.5 | 1.92 | 83~86 | >98 |
| 0.2 | 1.0 | 0.5 | 1.92 | 88~92 | >98 |

As shown in Table 6, the conversion of acetone into DMEC is improved as the LHSV decreases, that is, as the reaction time is increased. The LHSV useful for the continuous production of acetylene alcohol compounds according to the present invention ranges preferably from 0.2 to 4.0.

EXAMPLE IV
Effect of Ion Exchange Resin Type

In the Example, experiments were performed to determine the nature of the ion exchange resin can influence the continuous ethynylation process of the invention. Strongly basic anion exchange resins, especially strongly basic quaternary ammonium hydroxide anion exchange resins, were selected. The strongly basic quarternary ammonium hydroxide anion exchange resins suitable for use in the process of the present invention are those in which a nitrogen atom is attached to three alkyl groups and to a methylene group, and the methylene group is attached to a monocyclic aromatic group which is a constituent part of a cross-linked organic polymer or is attached to the phenyl group of poly-stylene resin, taking account of activity and physical stability. Of the cormercially available strongly basic anion exchange resins having such structures, IRA-402 (OH), IRA-900 (OH) and AB-17-8 (OH) are preferred.

For the test of these anion exchange resins, the continuous production of DMEC through condensation of acetone and acetylene was considered as a model reaction. The test was carried out at 40° C. under a pressure of 20 kg/cm$^2$ by using NMP or DMF as a solvent with the molar ratio of acetylene to acetone to the solvent being set to 1.0:0.5:1.92. The results according to anion exchange resin are given in Table 7, below, for LHSV=0.2, 1.0 and 4.0.

TABLE 7

| LHSV | Conversion Rate of Acetone (%) | | | Selectivity for DMEC (%) | | |
| --- | --- | --- | --- | --- | --- | --- |
| | AB-17-8 | IRA-402 | IRA-900 | AB-17-8 | IRA-402 | IRA-900 |
| 0.2 | 85–91 | 88–92 | 89–93 | >97 | >98 | >98 |
| 1.0 | 70–77 | 69–77 | 71–79 | >97 | >97 | >98 |
| 4.0 | 55–74 | 56–74 | 59–76 | >97 | >98 | >98 |

As apparent from Table 7, the three strongly basic anion exchange resins provide similar results, irrespective of their different identities. That is, the conversion rates of acetone and the selectivities for DMEC according to the resins are within an acceptable error range at a given LHSV, if the other conditions are maintained constant. Therefore, if the life span of the resin is not taken into account, the three resins, IRA-402 (OH), IRA-900 (OH) and AB-17-8 (OH), all are useful for the continuous ethynylation of the present invention.

EXAMPLE V
Production of Acetylene Alcohol Compounds by Continuous Process-1

In the above examples, the ethynylation conditions which efficiently produced acetylene alcohol compounds by condensing ketones and acetylene were found to include a strongly basic, quaternary ammonium hydroxide anion exchange resins such as IRA-402 (OH), IRA-900 (OH) and AB-17-8 (OH), an aprotic solvent such as DMF, NMP and DMSO, a molar ratio of acetylene to ketone to solvent of 1.0:0.2–3.0:1.0–4.0 and preferably 1.0:0.5–1.0:1.5–3.0, 40° C. for the reaction temperature, and 20 kg/cm$^2$ for the reaction pressure.

In this example, various ketones were used to produce acetylene alcohol compounds under the above conditions in a continuous process using the apparatus of FIG. 1.

The reaction temperature and pressure were fixed at 40° C. and 20 kg/cm$^2$. Acetylene was saturated in DMF and the reactant mixtures were passed through IRA-402 (OH). The results are given in Table 8, below.

TABLE 8

| Ke- | Molar Ratio | | | | | Conv. | Selec- tivity |
|---|---|---|---|---|---|---|---|
| tones | HC≡CH | Ketone | DMF | LHSV | Product | (%) | (%) |
| Acet. | 1.0 | 0.50 | 1.92 | 0.20 | DMEC | 88~92 | >98 |
| MH | 1.0 | 0.56 | 2.48 | 0.28 | DHL | 79~87 | >97 |
| GA | 1.0 | 0.53 | 2.48 | 0.30 | DHN | 79~83 | >99 |
| PT | 1.0 | 0.53 | 2.35 | 0.28 | DHiP | 85~98 | >99 |
| FA | 1.0 | 0.20 | 0.30 | 0.30 | GDHL | 75~80 | >99 |

As shown in Table 8, the conversion of ketone was maintained at a range of 75–90% regardless of the nature of the ketone when the ethynylation was carried out given reaction conditions with little variation of LHSV (0.2–0.3). That is, regardless of the molecular weight and chemical structure of the ketone used, similar results, including the conversion rate of the ketone and the selectivity for acetylene alcohol compounds, are obtained if the reaction conditions are consistent. Thus, similar, good results can be obtained with indifference to the ketone type provided that the molar ratio of the composition is appropriately maintained under given reaction conditions.

EXAMPLE VI
Production of Acetylene Alcohol Compounds in Continuous Process-2

This example pertains to the effect of solvent and acetylene solution selection. The same procedure as in Example V was repeated, except that NMP, instead of DMF, was used and the low temperature route was taken for the saturation of acetylene. The reactant mixtures were passed through ion exchange resin IRA-402 (OH). Results are given in Table 9, below.

TABLE 9

| Ke- | Molar Ratio | | | | | Conv. | Selec- tivity |
|---|---|---|---|---|---|---|---|
| tones | HC≡CH | Ketone | DMF | LHSV | Product | (%) | (%) |
| Acet. | 1 | 0.66 | 1.92 | 0.21 | DMEC | 83~90 | >98 |
| MH | 1 | 0.5 | 2.63 | 0.14 | DHL | 75~85 | >98 |
| GA | 1 | 0.28 | 1.50 | 0.17 | DHN | 85~88 | >99 |
| PT | 1 | 0.49 | 1.96 | 0.25 | DHiP | 80~88 | >99 |

As shown in Table 9, similar results were obtained even when the solvent was changed from DMF to NMP and the acetylene was differently saturated. That is, the conversion rates of ketones and the selectivities for corresponding acetylene alcohol compounds were similar to those of Example V. Therefore, these results confirm again that the method for producing acetylene alcohol compounds in a continuous process, according to the present invention, brings about similar results regardless of the kind of solvents used and the method of acetylene saturation.

EXAMPLE VII
Reaction Temperature Effect-1

In this example, the influence of reaction temperature on the continuous ethynylation of the present invention was investigated. Generally, the temperature for the ethynylation should be below the maximum temperature at which strongly basic anion exchange resins can work. Thus, experiments were carried out at 20° C., 30° C. and 40° C., while the conversion rates of ketone was monitored over time in a given reaction condition. For this, the LHSV was set to 4, a very severe condition, because low values of LHSV, although they allow high conversion rates of ketones, require too much time consumption in obtaining information for reaction tendencies. DMEC production through the condensation of acetylene to acetone was adopted as a model reaction. Ethynylation was performed by passing the reactant mixtures through anion exchange resin IRA-402 (OH) at 30° C. and 40° C. The conversion rates according to time were monitored and the results are shown in FIG. 2.

Figure 2:
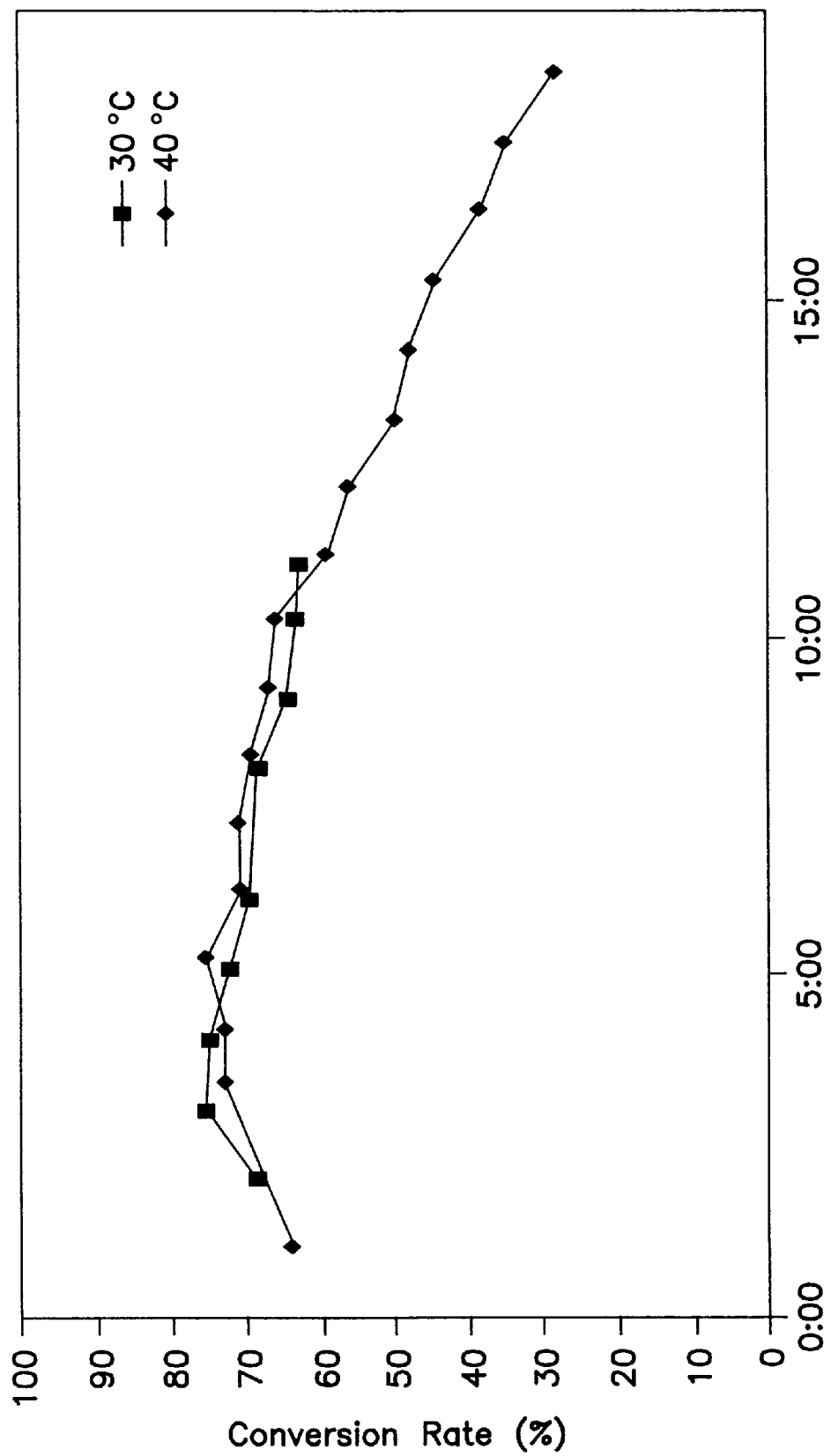
FIG. 2 is a graph showing the conversion rate of acetone plotted against times in accordance with Example VII.

Referring to FIG. 2, the 30° C. and 40° C. conversion rate curves both are in the range of 65–75% for the first 10 hours. Thereafter, the conversion rates gradually decrease with a greater decline at 40° C. than at 30° C. That is, after 10 hours, more acetone is converted to DMEC at 30° C. than at 40° C. The anion exchange resin IRA-402 (OH) may be used in the temperature range of 30–40° C., but 30° C. is better when taking the anion exchange resin's capacity for maintaining activity.

EXAMPLE VIII
Reaction Temperature Effect-2

The same procedure as in Example VII was repeated, except that IRA-900 (OH), instead of IRA-402 (OH), was used. The conversion rates at 20° C., 30° C. and 40° C. were plotted against time. The results are given in FIG. 3.

Figure 3:
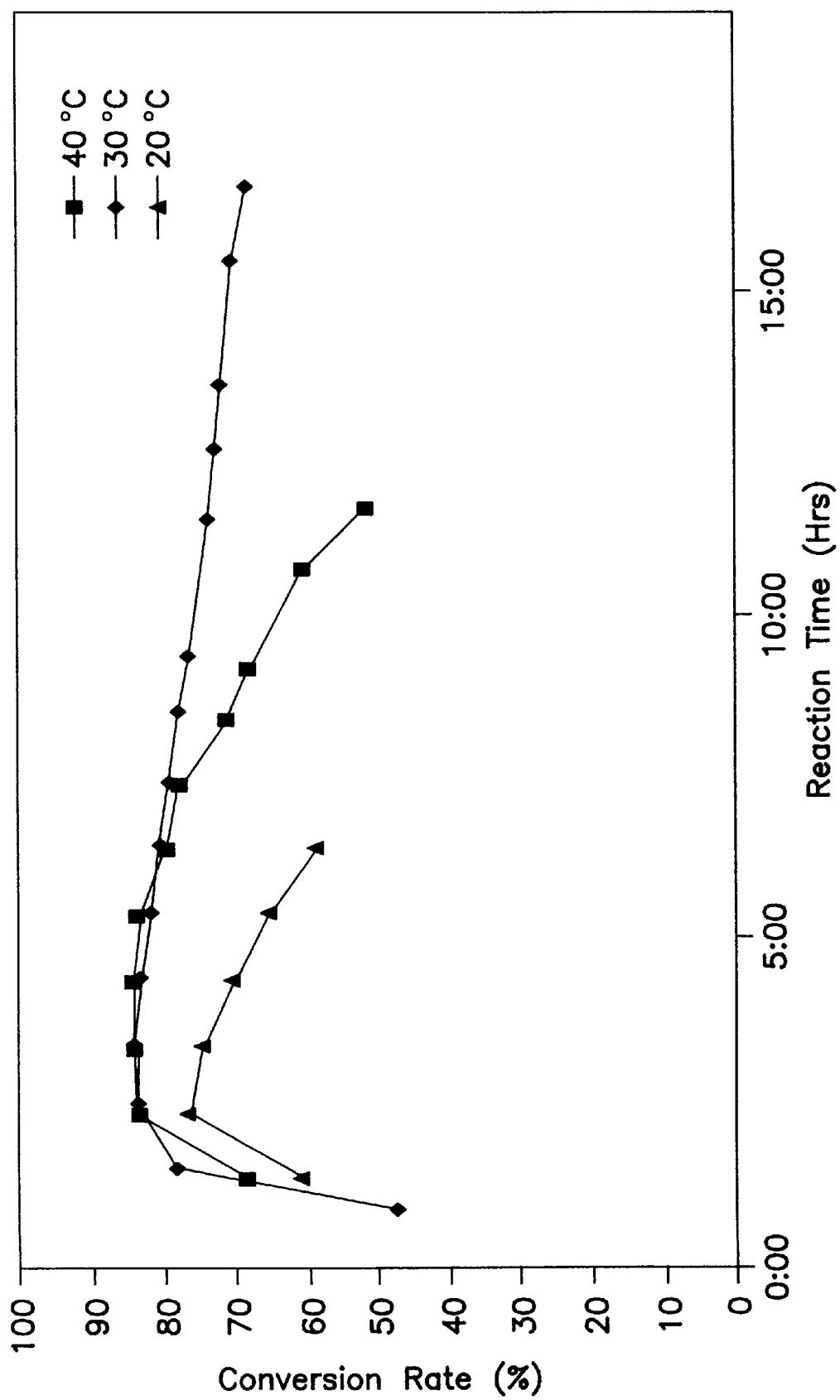
FIG. 3 is a graph showing the conversion rate of acetone plotted against times in accordance with Example VIII.

With reference to FIG. 3, the 30° C. and 40° C. conversion rate curves show the same behavior as the IRA-402 (OH) curves of Example VII. The conversion rate of acetone was maintained at 65–75% for 10 hours after reaction initiation. Thereafter, the conversion rate of acetone at 30° C. gradually decreased, while the 40° C. curve showed a sharp drop. For 20° C., the early conversion rate of acetone is lower (55–65%), compared with the rate at 30° C. and 40° C. Moreover, the early acetone conversion rate could be maintained for only 3 hours or less. After that time, the conversion rate dropped sharply. Therefore, the anion exchange resin IRA-900 (OH) may be used in the temperature range of 30–40° C., but 30° C. is better when taking into account the anion exchange resin's capacity for maintaining activity.

EXAMPLE IX
Test for Life Time of Ion Exchange Resin-1

The anion exchange resin useful lifetime in the ethynylation of acetylene and ketone in accordance with the present invention, that is, the time over which the resin can maintain a desired ketone conversion rate, is very important for commercial application of the present invention. Anion exchange resins IRA-402 (OH), IRA-900 (OH) and AB-17-8 (OH) were tested to determine how long they could maintain useful activity, that is, their available life time, when they were regenerated. Tests were executed under severe treatment conditions (LHSV=4) and under optimal treatment conditions (LHSV=0.2).

Under the conditions given in Table 10, below, anion exchange resin IRA-402 (OH) was used for the ethynylation of acetylene and acetone.

TABLE 10

| Molar Ratio | | | | Temp. | Press. |
|---|---|---|---|---|---|
| HC≡CH | Acetone | NMP | LHSV | (° C.) | (Kg/cm$^2$) |
| 1 | 0.5 | 2.37 | 0.2 | 40 | 20 |

Figure 4:
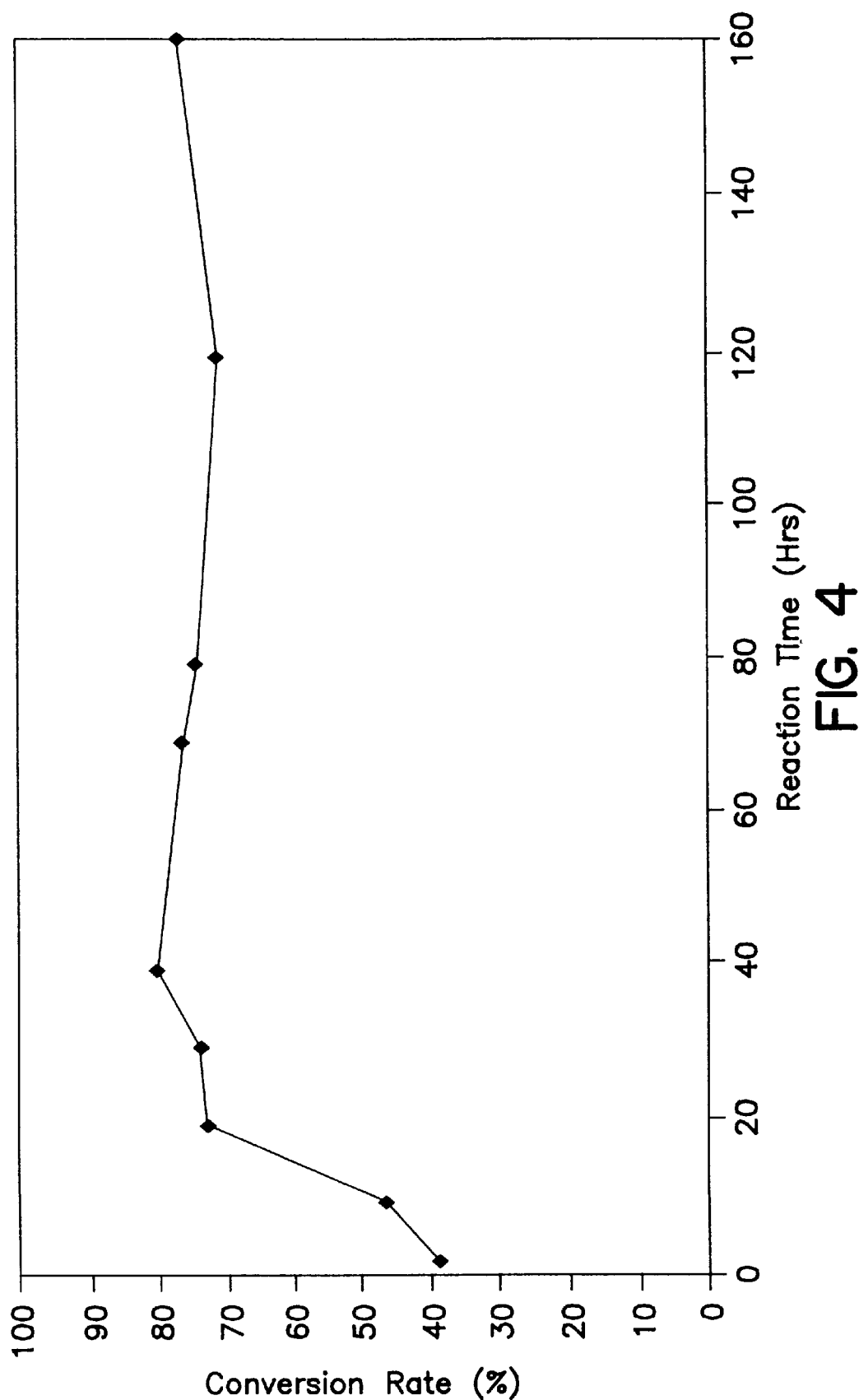
FIG. 4 is a graph showing the conversion rate of acetone plotted against times in accordance with Example IX.

The curve in FIG. 4 shows the change in conversion rate with reaction time when using IRA-402 (OH). As shown in FIG. 4, the conversion rate of acetone was stably maintained at above 75% for about 160 hours at LHSV=0.2. After 160 hours, the conversion rate of acetone decreased below 65%. At this time, the resin underwent the same regeneration as in the above Regeneration Example, and was reused. No noticeable difference in the early conversion rate was shown before and after the regeneration. The early conversion rate was still retained by the resin, which underwent the regeneration procedure several times. The ethynylation was effectively performed for about 1,500 hours.

EXAMPLE X
Test for Life Time of Ion Exchange Resin-2

As experienced in Example IX, the study on the anion exchange resin lifetime at LHSV=0.2 is time consuming. In this example, the ethynylation was performed under the severe condition of LHSV=4.0. The reaction conditions are given in Table 11, below.

TABLE 11

| Molar Ratio | | | | Temp. | Press. |
| --- | --- | --- | --- | --- | --- |
| HC≡CH | Acetone | NMP | LHSV | (° C.) | (Kg/cm$^2$) |
| 1 | 0.5 | 1.92 | 4.0 | 40 | 20 |

Figure 5:
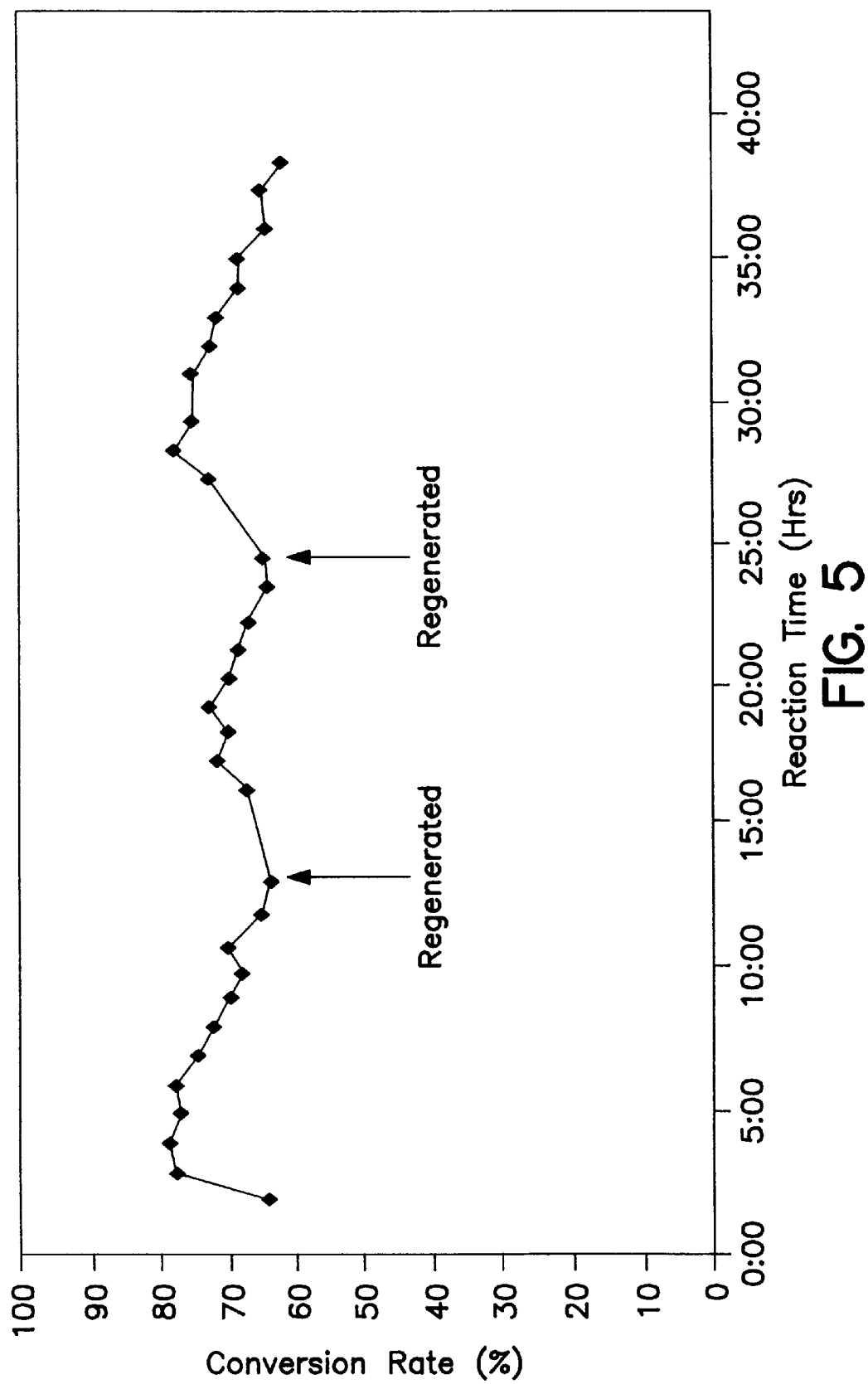
FIG. 5 is a graph showing the conversion rate of acetone plotted against times in accordance with Example X.

The results are shown in FIG. 5. The conversion rate of acetone was maintained at about 65–75% for 10 hours. This is almost consistent with the result in FIG. 4. The 10 hour resin lifetime at LHSV=4.0 is in proportion to the lifetime (about 160 hours) of Example IX (LHSV=0.2).

At the point that the acetone conversion rate fell to about 65%, the anion exchange resin was regenerated in the same manner as in the above Example and subsequently tested for activity. The anion exchange resin could maintain its activity for 50 hours or more through four regenerations. Even after the fourth regeneration, the resin could be regenerated twice more to a 55–65% activity level for 20 additional hours of resin activity.

EXAMPLE XI
Test for Life Time of Ion Exchange Resin-3

Figure 6:
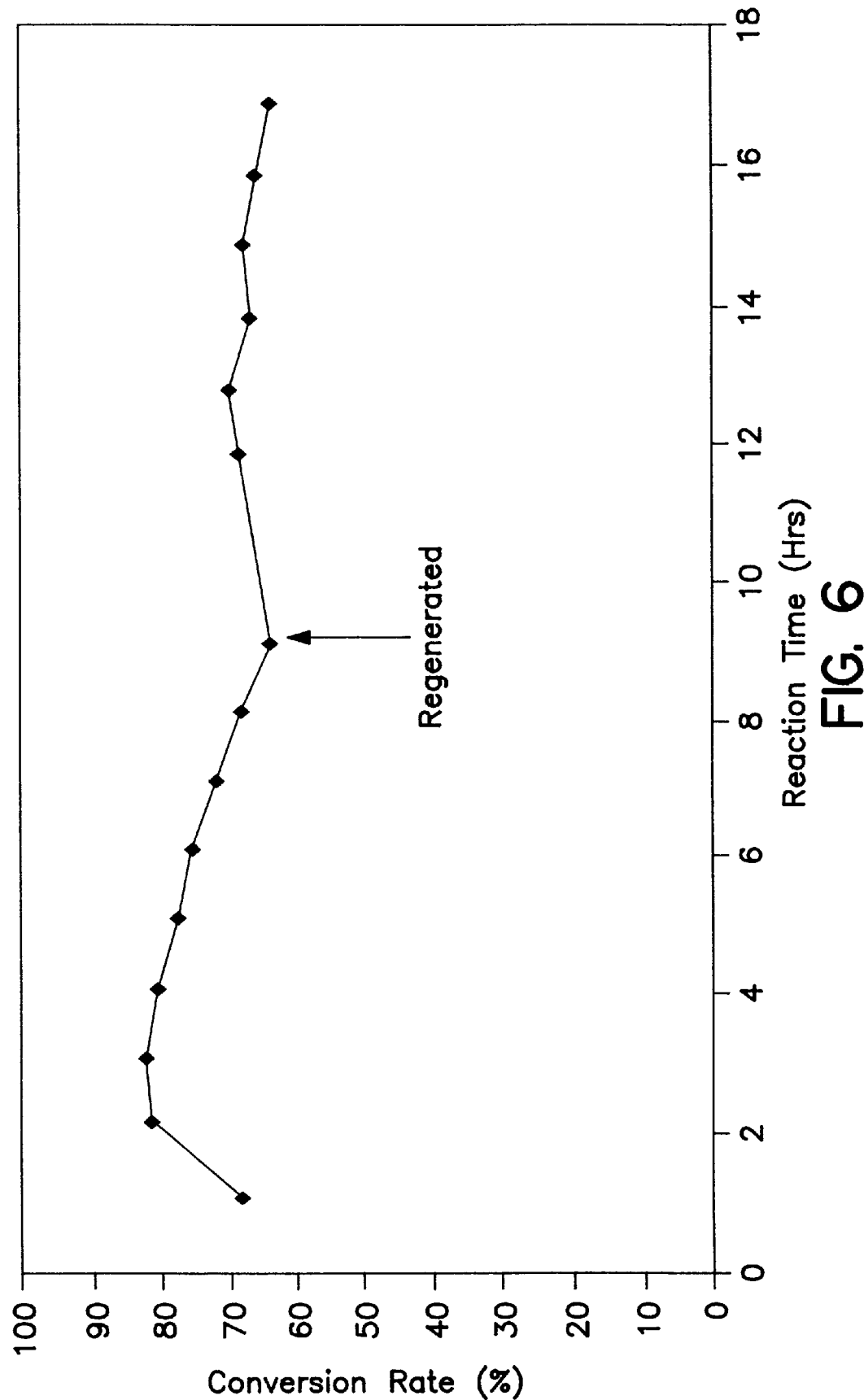
FIG. 6 is a graph showing the conversion rate of acetone plotted against times in accordance with Example XI.

Ethynylation was carried out in a similar manner to that of Example X, except that IRA-900 (OH) was used instead of IRA-402 (OH). The results are given in FIG. 6.

Compared to IRA-402 (OH), IRA-900 (OH), has a similar catalyst life time, but maintains a longer period over which the early conversion rate of acetone is maintained through regeneration. Via nine rounds of regeneration, the IRA-900 (OH) maintained 65–75% activity for about 100 hours in total. This maintenance time is twice as long as that of IRA-402 (OH). Therefore, IRA-900 (OH) is more efficient for use in the invention than IRA-402 (OH).

EXAMPLE XII
Test for Life Time of Ion Exchange Resin-4

In this example, MH was used as a ketone reactant to produce DHL, while AB-17-8 (OH) was selected as an anion exchange resin. Ethynylation via a continuous process was carried out under the conditions indicated in Table 12, below.

TABLE 12

| Molar Ratio | | | | Temp. | Press. |
| --- | --- | --- | --- | --- | --- |
| HC≡CH | MH | NMP | LHSV | (° C.) | (Kg/cm$^2$) |
| 1 | 0.5 | 2.63 | 0.15 | 40 | 20 |

Figure 7:
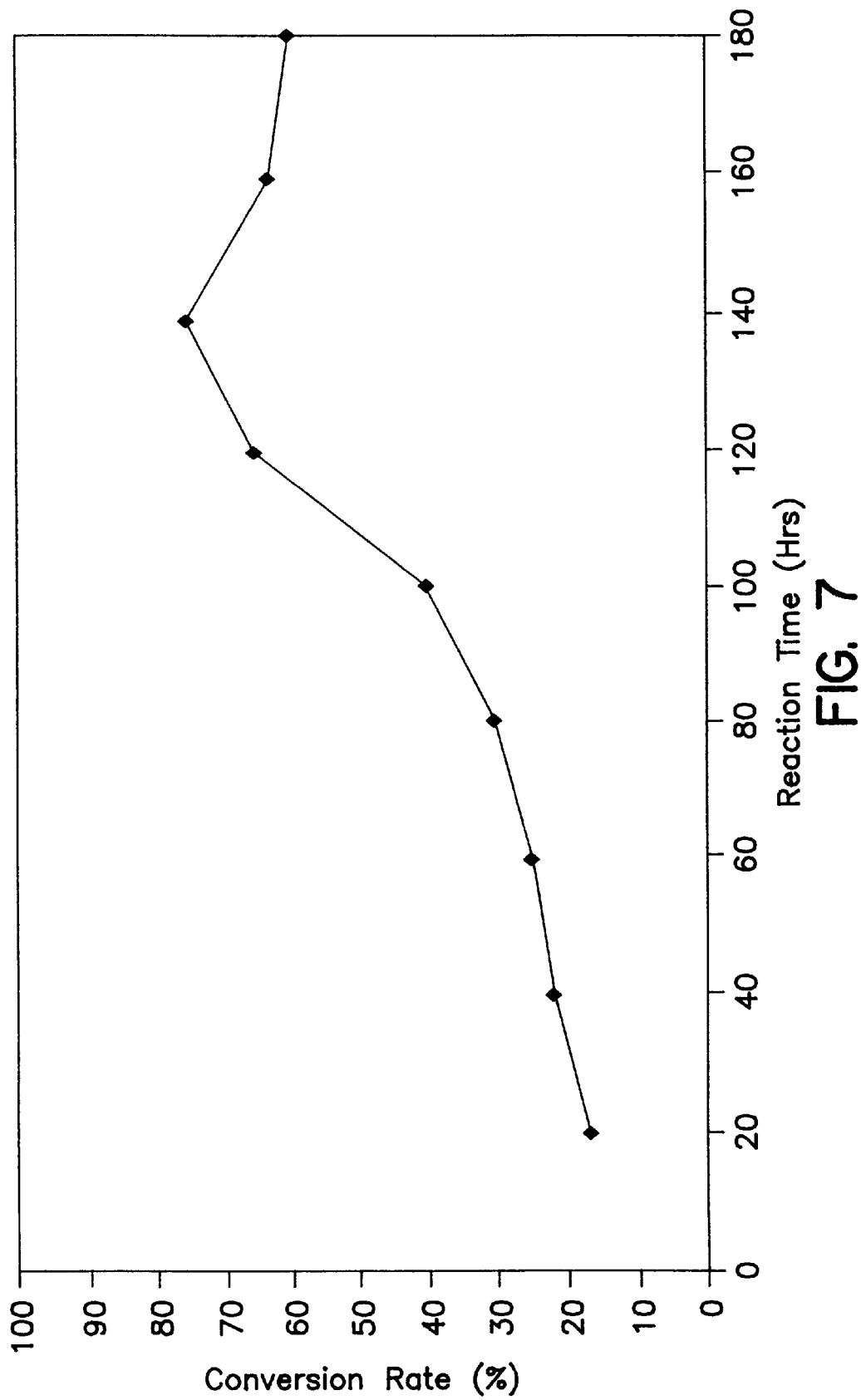
FIG. 7 is a graph showing the conversion rate of MH plotted against times in accordance with Example XII.

The results are shown in FIG. 7. As shown in FIG. 7, the conversion rate of MH increased to 78–80% at 150 hours. From this point, the conversion rate gradually decreased to about 63%. At this point, the reactant feed mixture was stopped, and the resin was regenerated. Resumption of the process showed that the regenerated resin attained and maintained its previous conversion rate.

EXAMPLE XIII
Test for Life Time of Ion Exchange Resin-5

In this example, GA was used as a ketone reactant to produce DHN, while AB-17-8 (OH) was selected as an anion exchange resin. Ethynylation via a continuous process was carried out under the conditions indicated in Table 13, below.

TABLE 13

| Molar Ratio | | | | Temp. | Press. |
| --- | --- | --- | --- | --- | --- |
| HC≡CH | GA | NMP | LHSV | (° C.) | (Kg/cm$^2$) |
| 1 | 0.25 | 1.61 | 0.18 | 40 | 20 |

Figure 8:
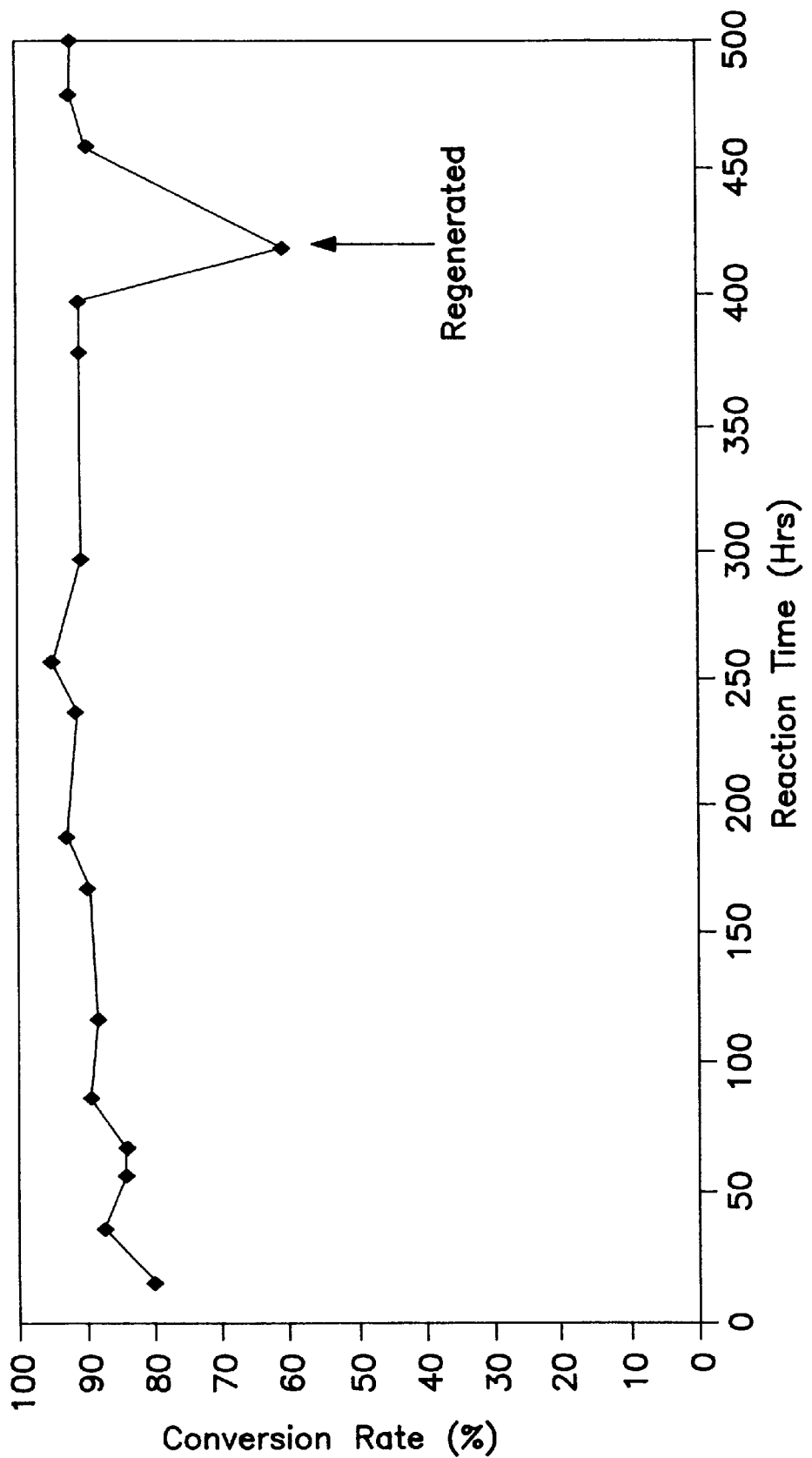
FIG. 8 is a graph showing the conversion rate of GA plotted against times in accordance with Example XIII.

The results are shown in FIG. 8. As shown in FIG. 8, the conversion rate of GA was maintained at 80 to 85% for 300 hours or more. As the conversion rate gradually decreased after that point, the anion exchange resin was regenerated, and the reactant mixture was reintroduced. Resumption of the process showed that the regenerated resin attained and maintained its early conversion rate. The ethynylation can be continuously performed without replacing the resin with fresh resin.

EXAMPLE XIV
Test for Life Time of Ion Exchange Resin-6

In this example, PT was used as a ketone reactant to produce DHiP while AB-17-8 (OH) was selected as an anion exchange resin. Ethynylation via a continuous process was carried out under the conditions indicated in Table 14, below.

TABLE 14

| Molar Ratio | | | | Temp. | Press. |
| --- | --- | --- | --- | --- | --- |
| HC≡CH | PT | NMP | LHSV | (° C.) | (Kg/cm$^2$) |
| 1 | 0.25 | 1.61 | 0.25 | 40 | 15 |

The conversion rate of GA was maintained at 80% or higher for 160 hours. As the conversion rate gradually decreased from that point, the anion exchange resin was regenerated, after which the reactant mixture was reintroduced. Resumption of the process showed that the regenerated resin was increased in the early conversion rate range. Therefore, the ethynylation can be continuously performed without replacing the resin with fresh resin.

As described hereinbefore, commercially valuable acetylene alcohol compounds can be produced at high yield in an environmentally favorable fashion by condensing acetylene to ketones in an aprotic solvent in the presence of a heterogeneous, strongly basic, quaternary ammonium hydroxide anion exchange resin. For successful and efficient ethynylation of acetylene with ketones containing the group —CH$_2$COCH$_2$—, preferable molar ratios of acetylene to ketone to solvent are in the range of 1.0:0.2–3.0:1.0–4.0. Experiments at temperatures in the range of 20 to 50° C. showed that desirable ketone conversion rates and acetylene alcohol selectivities are obtained at 30 to 40° C. The pressure may range from 10 to 30 kg/cm$^2$. NMP, DMF and DMSO are effective as the aprotic solvent and all give similar results. Ethynylation was carried out at LHSV (defined as the volume of the reactant passed through the unit volume of anion exchange resin) in the range of 0.1 to 5.0. Data was obtained showing that an LHSV of 0.2 to 4.0 is preferred. In order to carry out the production of acetylene alcohol compounds in a continuous process, two or more batches of the anion exchange resins are employed: one batch of the strong basic, heterogeneous quaternary ammonium hydroxide anion exchange resin is operated while the other batch is regenerated with the aid of an alkali methanol solution. The regenerated resin is restored to its original activity level. Consequently, commercially useful acetylene alcohol compounds can be continuously produced at high conversion rates with high selectivity therefor, according to the present invention.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for producing an acetylene alcohol compound in a continuous process, comprising the steps of:
   (i) saturating an acetylene gas in an aprotic solvent selected from the group consisting of dimethylformamide, dimethyl sulfoxide and N-methylpyrrolidone in a first reactor in the absence of liquid ammonia and alkali metal hydroxide;
   (ii) mixing the saturated acetylene solution with a ketone containing a —CH$_2$CHOCH$_2$— to form a reactant mixture of said acetylene, ketone and solvent in a molar ratio of 1.0:0.2–3.0:1.0–4.0;
   (iii) feeding the reactant mixture into one of a second and third reactor, said second and third reactors containing a strongly basic quaternary ammonium hydroxide anion exchange resin, at a liquid hourly space velocity in the range of 0.1 to 5.0; and
   (iv) reacting the reactant mixture in the presence of said resin at a temperature of about 20 to 50° C. under a pressure of about 10 to 30 kg/cm$^2$;

said second and third reactors being alternately operated to permit the regeneration of said resin in one reactor while said other reactor is being operated.

2. The method as set forth in claim 1, wherein said quaternary ammonium hydroxide anion exchange resin has a chemical structure in which each nitrogen atom is attached to three alkyl groups and to a methylene group, the methylene group being attached to a monocyclic aromatic group which is a constituent part of a cross-linked organic polymer.

3. The method as set forth in claim 1, wherein said quaternary ammonium hydroxide anion exchange resin has a chemical structure in which each nitrogen atom is attached to three alkyl groups and to a methylene group, the methylene group being attached to the phenyl of a polystyrene resin.

4. The method as set forth in claim 1, wherein said temperature ranges from 30 to 40° C.

5. The method as set forth in claim 1, wherein said pressure ranges from 15 to 25 kg/cm$^2$.

6. The method as set forth in claim 1, wherein said molar ratio of acetylene to ketone to solvent in the reactant mixture is in the range 1.0:0.5–1.0:1.5–3.0.

7. The method as set forth in claim 1, wherein said reactant mixture is fed at a liquid hourly space velocity in the range of 0.2–4.0.

8. The method as set forth in claim 1, wherein said ketone is represented by formula II:

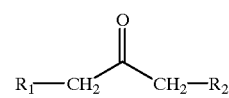

II wherein R$_1$ and R$_2$, which may be the same or different, are selected from the group consisting of hydrogen; linear or branched, saturated or unsaturated alkyl containing 1 to 16 carbon atoms; and linear or branched, saturated or unsaturated phenyl containing 1 to 16 carbon atoms.

9. The method as set forth in claim 8, wherein said ketone is selected from the group consisting of 2-propanone, 6-methyl-hep-5-en-2-one, 6,10-dimethyl-undeca-5,9-dien-2-one, 6,10,14-trimethyl-5,9,13-pentadecartrien-2-one, and 6,10,14-trimethyl-pentadecan-2-one.

10. The method as set forth in claim 1, wherein said acetylene alcohol compound is selected from the group consisting of 2-methyl-but-3-yn-2-ol, 3,7-dimethyl-oct-6-en-1-yn-3-ol, 3,7,11-trimethyl-dodeca-6,10-dien-1-yn-3-ol, 3,7,11,15-tetramethyl-6,10,14-hexadecatrien-1-yn-3-ol and 3,7,11,15-tetramethyl-hexadeca-1-yn-3-ol.

11. The method as set forth in claim 1, wherein said anion exchange resin is treated with a solution of NaOH or KOH in methanol to regenerate the resin.

* * * * *